United States Patent [19]

Wong et al.

[11] Patent Number: 5,505,828

[45] Date of Patent: *Apr. 9, 1996

[54] CALIBRATION SOLUTIONS USEFUL FOR ANALYSIS OF BIOLOGICAL FLUIDS AND METHODS EMPLOYING SAME

[75] Inventors: David K. Wong, Del Mar; Kenneth M. Curry, Oceanside, both of Calif.

[73] Assignee: Via Medical Corporation, San Diego, Calif.

[*] Notice: The term of this patent shall not extend beyond the expiration date of Pat. No. 5,330,634.

[21] Appl. No.: 379,555

[22] PCT Filed: Aug. 26, 1993

[86] PCT No.: PCT/US93/08109

§ 371 Date: Feb. 2, 1995

§ 102(e) Date: Feb. 2, 1995

[87] PCT Pub. No.: WO94/06019

PCT Pub. Date: Mar. 17, 1994

Related U.S. Application Data

[63] Continuation-in-part of Ser. No. 937,980, Aug. 28, 1992, Pat. No. 5,330,634.

[51] Int. Cl.$^6$ ........................ G01N 27/26
[52] U.S. Cl. ............... 205/777.5; 204/403; 204/409; 204/412; 204/416; 204/419; 204/433; 128/635; 128/760; 205/779; 205/781.5; 205/782; 205/787.5
[58] Field of Search ................ 204/153.12, 403, 204/409, 412, 416, 419, 153.1; 128/632, 635, 760; 604/4

[56] References Cited

U.S. PATENT DOCUMENTS

| | | | |
|---|---|---|---|
| 3,616,409 | 10/1971 | Tosteson | 204/409 |
| 3,661,010 | 5/1972 | Neuwelt | 70/61 R |
| 3,763,850 | 10/1973 | Gaudebout et al. | 128/2 E |
| 4,340,457 | 7/1982 | Kater | 204/416 |
| 4,450,064 | 5/1984 | Harman, III | 204/412 |
| 4,461,998 | 7/1984 | Kater | 204/416 |
| 4,492,622 | 1/1985 | Kuypers | 204/403 |
| 4,516,580 | 5/1985 | Polanyi | 128/632 |
| 4,535,786 | 8/1985 | Kater | 204/403 |
| 4,571,292 | 2/1986 | Liu et al. | 204/412 |
| 4,573,968 | 3/1986 | Parker | 604/67 |
| 4,734,184 | 3/1988 | Burleigh et al. | 204/409 |
| 4,736,748 | 4/1988 | Nakamura et al. | 128/632 |
| 4,786,394 | 11/1988 | Enzer et al. | 204/403 |
| 4,874,500 | 10/1989 | Madou et al. | 204/412 |
| 4,909,908 | 3/1990 | Ross et al. | 204/403 |
| 4,911,549 | 3/1990 | Karkar | 128/633 |
| 5,132,000 | 7/1992 | Sone et al. | 204/416 |
| 5,165,406 | 11/1992 | Wong et al. | 204/409 |
| 5,194,445 | 3/1993 | Satoh et al. | 514/474 |
| 5,330,634 | 7/1994 | Wong et al. | 204/409 |

*Primary Examiner*—Bruce F. Bell
*Attorney, Agent, or Firm*—Pretty, Schroeder, Brueggemann & Clark; Stephen E. Reiter

[57] ABSTRACT

Novel calibration solutions are provided which are useful, for example, with sensor assemblies used for analysis of $CO_2$, and optionally, for concurrent analysis of $O_2$, especially in combination infusion fluid delivery/blood chemistry analysis systems which include a sensor assembly with each of the assembly electrodes mounted in an electrode cavity in the assembly. The analysis system used in the practice of the present invention typically includes provision for delivering infusion fluid and measuring blood chemistry during reinfusion of the physiological fluid at approximately the same flow rates. The invention calibration solutions are useful for calibrating an array of sensors capable of simultaneously measuring a number of blood chemistry parameters, including the partial pressures (tensions) of carbon dioxide and oxygen, pH (hydrogen ion), sodium, potassium, ionized calcium, ionized magnesium, chloride, glucose, lactate and hematocrit, in body fluids. More particularly, this invention relates to the use of an infusible intravenous solution to facilitate calibration on a regular basis for every individual sensor in a sensor assembly, which is in constant fluid communication with the body regardless of whether the sensors are ex vivo or in vivo.

16 Claims, 2 Drawing Sheets

CALIBRATION SOLUTIONS USEFUL FOR ANALYSIS OF BIOLOGICAL FLUIDS AND METHODS EMPLOYING SAME

This application is a continuation-in-part of U.S. Ser. No. 07/937,980, filed Aug. 28, 1992, now issued as U.S. Pat. No. 5,330,634.

This invention relates to the diagnostic testing of body fluids, typically in conjunction with the infusion of fluids. In a particular aspect, the invention relates to calibration solutions useful with low-cost, disposable, sensor assemblies used in automated bedside monitors.

BACKGROUND OF THE INVENTION

Low-cost, disposable, electrochemical electrode assemblies have special utility as part of infusion fluid delivery systems commonly used in hospital patient care. Such systems infuse nutrients, medications, and the like directly into the patient at a controlled rate and in precise quantities for maximum effectiveness. Infusion fluid delivery systems are connected to a patient at an intravenous (IV) port, in which a hollow needle/catheter combination is inserted into a blood vessel of the patient and thereafter an infusion fluid is introduced into the vessel at a controlled rate, typically using a peristaltic pump. Blood chemistry monitoring systems that are combined with infusion delivery systems of this kind use the IV port to periodically withdraw a blood sample, perform measurements of blood ion concentrations and the like, and then discard the blood or reinfuse it into the patient. The system then resumes delivery of the infusion fluid.

Such combined infusion fluid delivery and blood chemistry monitoring systems include an infusion line and catheter through which the infusion fluid is provided to the patient and blood samples are withdrawn. The infusion line incorporates an electrode assembly having electrochemical sensors that are periodically exposed to the blood samples and thereby provide electrical signals to an analyzer for conversion into corresponding blood chemistry data. A control unit periodically halts delivery of the infusion fluid for a brief interval, during which time a blood sample is withdrawn from the patient into the infusion line and routed to the electrode assembly, which then generates the electrical signals. After the electrical signals have been received by the analyzer, the control unit disposes of the blood or reinfuses the blood sample into the patient, and the flow of infusion fluid is resumed.

The electrode assembly typically, among other types of electrochemical sensors, includes a reference electrode and a plurality of sensing electrodes (sensors) that are each sensitive to a particular ion or species of interest. All of the electrodes are typically embedded in the base of the electrode assembly. For example, ion-sensitive electrodes (ISE) generate electrical signals only in response to contact with the particular ion to which they are sensitive, and therefore provide selective measurement of the amount of that ion in the blood. This type of sensing electrode can be provided to measure, for example, blood calcium, hydrogen ion, chloride, potassium, and sodium. In a differential measurement system, the reference electrode might be another ion-selective electrode (e.g., a chloride or sodium electrode) that is continuously exposed to a calibration or reference fluid. Alternatively, in a non-differential measurement system, a conventional reference electrode (which maintains a fixed potential when exposed either to reference fluid or to analyte) is required.

In a differential measurement system, during the delivery of calibration fluid, the calibration fluid flows past both the reference electrode and the sensing electrodes, and the electrical potential between the reference electrode and each sensing electrode is measured. This provides a calibration measurement of the electrode assembly. During a subsequent blood chemistry measurement, a blood sample is drawn into the electrode assembly, where it comes into contact with the sensing electrodes, but not the reference electrode. The electrical potential between the reference electrode and each sensing electrode is measured again and compared with the earlier calibration measurement to provide an indication of the ion concentration in the blood of the particular ion to which the sensing electrode is sensitive. After measurement is completed, the blood sample is discarded or reinfused from the electrode assembly back into the patient, and delivery of infusion fluid is resumed.

Presently employed electrochemical sensors for clinical diagnostic applications can be divided into three categories: potentiometric, amperometric and ac impedance. For example, hematocrit (Hct), which is defined as the volume percent of red cells in the blood, can be determined by measuring the ac impedance of the blood with a pair of metal electrodes, typically at 1 kilohertz (kHz).

An amperometric sensor correlates the concentration of a specific component of interest to a current output. Typically, oxygen partial pressure (pO$_2$) and glucose (Glu) are determined with amperometric sensors. An oxygen sensor assembly usually consists of a noble metal (e.g., platinum or gold) working electrode and a suitable counter electrode (e.g., silver/silver chloride). An oxygen permeable, but liquid impermeable, membrane is usually mounted over the sensor assembly to separate the sample from the internal electrolyte to avoid contamination. The sensor measures the limiting current of oxygen reduction at the working electrode according to the following equation:

$$O_2 + 2H_2O + 4e \rightarrow 4OH^-$$

This is accomplished by applying a bias voltage of approximately 700 mV between the working (negative) electrode and the counter (positive) electrode. This is also known as a Clark electrode. The current passing between these two electrodes is proportional to the pO$_2$ level in the sample.

The glucose sensor is very similar in construction to an oxygen sensor. The difference is that a hydrophilic membrane with immobilized glucose oxidase is used instead of the hydrophobic oxygen membrane. In the presence of glucose oxidase (GOD), the following reaction takes place:

$$Glucose + O_2 \rightarrow Gluconic\ Acid + H_2O_2$$

In this case, glucose concentration can be determined by either polarizing the working electrode anodically or cathodically by approximately 700 mV to measure the rate of hydrogen peroxide oxidation or oxygen reduction, respectively.

A potentiometric sensor provides a voltage change which is related to the species of interest. Ionic species, such as hydrogen ion (H$^+$), sodium (Na$^+$), potassium (K$^+$), ionized calcium (Ca$^{++}$) and chloride (Cl$^-$), are commonly measured by ion selective electrodes (ISE), a typical class of potentiometric sensors. The commonly used CO$_2$ sensor, better known as the Severinghaus electrode, is also a potentiometric sensor (and is, in fact, essentially a modified pH sensor). Typically, it consists of a pH electrode and a reference electrode with both covered by a hydrophobic (gas permeable-liquid impermeable) membrane such as silicone. There is a thin layer of weakly buffered internal electrolyte (e.g., 0.001M $NaHCO_3$) between the hydrophobic membrane and the pH sensing membrane. Carbon dioxide in the sample eventually reaches equilibrium with the internal electrolyte and produces a pH shift as a result of the following equation:

$$CO_2 + H_2O \rightarrow H^+ + HCO_3^-$$

The resulting pH shift is then measured by the pH electrode. Therefore, there is a direct relationship between the $CO_2$ partial pressure ($pCO_2$) in a sample and the pH thereof.

The accuracy of measurement obtained with any of the above-described sensors can be adversely affected by drift, particularly after exposure to biological fluids such as whole blood. Therefore, frequent calibration is required. This is particularly true for gases such as $pO_2$ and $pCO_2$ because any change in the gas transport properties of the membrane may affect the sensor output. To this end, a number of calibration fluids are usually needed. This is because at least two different calibrant concentration levels are usually required to characterize a sensor. For a multi-parameter system, it is sometimes not possible to use the same two solutions to calibrate all sensors due to concerns such as chemical incompatibility and long term stability. Moreover, since it is technically very difficult to maintain $pCO_2$ and $pO_2$ constant at desired calibration levels, most conventional blood chemistry analyzers carry two gas cylinders and several bottles of reagents just to fulfill the calibration requirements. This makes the system bulky and cumbersome to use.

An attempt was made to fill pre-tonometered liquid calibrants sealed into aluminum foil pouches under partial vacuum as calibrants, as described by Burleigh (U.S. Pat. No. 4,734,184). This approach substantially reduced the size, and improved the portability of blood chemistry analyzers. However, the contents of the pouch have a limited life once the pouch is opened.

The current trend is to move away from bench top analyzers towards the use of bedside analytical systems. Moreover, instead of taking samples from the patients, sensors are either miniaturized and inserted into a blood vessel (in vivo) or constructed as part of a flow cell connected to the patient end of an existing vascular access port (ex vivo) to provide continuous monitoring of blood chemistry.

The in vivo approach is conceptually more attractive because it provides continuous results without intervention. However, it is much more difficult to implement in practice. The major hurdle is, of course, the blood clotting problem. Blood compatibility has always been a challenging issue. Even with a short term solution in hand, once sensors are placed in the blood stream, repeated calibration becomes very difficult.

The ex vivo approach, originally described by Parker (U.S. Pat. No. 4,573,968), employs a control unit to periodically withdraw a small amount of blood to come in contact with sensors (which are incorporated into an in-line flow cell) when a reading is desired. After a measurement is taken, the control unit resumes delivering physiological saline into the blood vessel. As a result, the blood drawn is effectively flushed back into the patient and the sensors are washed clean. Kater (in U.S. Pat. No. 4,535,786) discloses a method to use an infusible intravenous (I.V.) saline solution to calibrate ionic species in the biological fluid. However, Kater does not address the calibration of species such as glucose, $pO_2$, and $pCO_2$, as contemplated by the present invention.

As previously indicated, all blood chemistry sensors require frequent calibration in order to maintain the accuracy of measurement. In a multi-parameter bench top analyzer system, it often requires more than one calibration fluid (and/or gas) to accomplish this task. In an ex vivo blood chemistry monitor, it is much more desirable to use a single calibration solution for all the sensors, and to flush the sensors clean. In a multi-parameter ex vivo system, such as the VIA 1-01 Blood Chemistry Monitor (available from Via Medical Corporation, San Diego, Calif.), i.e., a system that measures one or more of $Na^+$, $K^+$, $Ca^{++}$, $Mg^{++}$, pH, $pCO_2$, $pO_2$, glucose, lactate and hematocrit, this requirement becomes very demanding.

In particular, the calibration of pH and $pCO_2$ remains a challenge. In an aqueous solution, these two parameters are inter-related by the following equation:

$$CO_2 + H_2O \rightarrow H^+ + HCO_3^-$$

At 37° C., the pH in a simple bicarbonate-containing solution is equal to $$6.10 + \log\{[HCO_3^-]/0.0301\ pCO_2\}$$

Since the normal $pCO_2$ in arterial blood is approximately 40 mmHg, while the atmosphere contains 0.2–0.5 mmHg of $CO_2$, atmospheric $CO_2$ levels are not only too low, but they are also too variable to serve as a calibration point. Hence, an external $CO_2$ source is required. Normally, the approach used in the art is to tonometer the solution with a known $CO_2$-containing gas, and then package the gas-equilibrated solution in a sealed container. This is not only costly but also requires considerable effort to demonstrate its safety as an infusible solution.

Although U.S. Pat. No. 4,736,748 (Nakamura) suggests that simultaneous calibration for $Na^+$, $K^+$, $Ca^{++}$, glucose and hematocrit, can be carried out with Ringer's Lactate having glucose added thereto, such a solution could not possibly be used for pH, $pCO_2$ and/or $pO_2$ calibration because the solution has no well defined pH value or $pO_2$ value, and contains essentially no $CO_2$. Indeed, since the amount of oxygen dissolved in Lactated Ringer's solution is not fixed (being a function of ambient temperature and barometric pressure—parameters which Nakamura does not contemplate monitoring), the reference does not teach how to use Lactated Ringer's solution as an oxygen calibrant. Moreover, the oxygen partial pressure in physiological saline is substantially higher than that in blood. It would be desirable for a calibration solution to have oxygen levels which are relatively close to physiological levels, regardless of what type of sensor is employed. Furthermore, Nakamura does not address measurement of hematocrit levels at all.

While Burleigh, supra., describes a solution which can be used for calibration of $CO_2$, the reference does not contemplate the use of an infusible calibrant, much less a substantially non-buffered, infusible calibrant. Indeed, the Burleigh $CO_2$ calibration solution would not be acceptable for infusion. In contrast to the practice of the present invention, after sample analysis, Burleigh directs assayed fluids into a waste collection reservoir. In accordance with the present invention, a very different analytical system is contemplated wherein sample withdrawn from a subject is reinfused after analysis. Thus, a different calibration solution is required for the practice of the present invention relative to what is taught in the art. Since Burleigh does not contemplate a substantially non-buffered, infusible calibrant, the reference provides no guidance as to suitable calibration solutions for use with combined infusion fluid delivery/blood chemistry measurement systems, as contemplated herein.

Sone et al., U.S. Pat. No. 5,132,000 (1992) is similar to Burleigh in that the reference describes solutions which can be used for calibration of $CO_2$-containing solutions. The reference does not, however, contemplate the use of an infusible calibrant. Similar to Burleigh, the Sone calibration solutions would not be acceptable for infusion. Successful analysis according to the Sone teaching requires the use of strong pH buffering. The level of buffering and ionic strength required by Sone clearly makes such solutions unacceptable for infusion.

From the discussion above, it should be apparent that there is a need for calibration solutions useful, for example, in combined infusion fluid delivery and blood chemistry measurement systems that allow accurate, reliable measurements of blood chemistry, that avoid the need for multiple calibration and/or reference solutions, and that are relatively easy to prepare by mixing injectable media that are readily available for patient use as "off-the-shelf" items. The present invention satisfies these needs.

BRIEF DESCRIPTION OF THE INVENTION

In accordance with the present invention, there are provided methods for the assay of $CO_2$ partial pressure ($pCO_2$), and optionally, $O_2$ partial pressure ($pO_2$), in physiological fluids. In addition, there are provided methods for the calibration of sensors employed for the detection of $pCO_2$, and optionally, $pO_2$. Further, there are provided calibration solutions suitable for use in the above methods. Presently preferred calibration solutions employed in the practice of the present invention include components necessary for the calibration of systems employed for the essentially simultaneous measurement of one or more of sodium ion concentration, potassium ion concentration, calcium ion concentration, magnesium ion concentration, hydrogen ion concentration, glucose concentrations, lactate concentrations, chloride concentrations, and hematocrit levels, in addition to carbon dioxide (and optionally, oxygen) partial pressures.

The invention provides simple means to prepare infusible calibration solutions, thereby eliminating the need for multiple calibration solutions, and increasing the measurement accuracy of blood chemistry analyses. In addition, the present invention provides improved assays employing the above-described infusible calibration solutions.

Other features and advantages of the present invention should be apparent from the following detailed description, which illustrates, by way of example, the principles of the invention.

DETAILED DESCRIPTION OF THE INVENTION

In accordance with the present invention, there is provided a method for the assay of $CO_2$ partial pressure ($pCO_2$), and optionally, $O_2$ partial pressure ($pO_2$), in physiological fluid, said method comprising
contacting an assembly having:
a fluid passageway and a sensor for $pCO_2$, and optionally a sensor for $pO_2$, exposed to said fluid passageway, and
means to pass physiological fluid and/or calibrant over said sensor,
with an infusion medium/calibrant comprising:
physiological sodium chloride-containing saline, and an amount of a suitable carbon dioxide source effective to provide a stable $CO_2$ partial pressure in the range of about 1 up to 100 mm Hg, and optionally a stable $O_2$ partial pressure in the range of about 0 up to 200 mm Hg; and calibrating said $CO_2$ sensor (and optionally, said $pO_2$ sensor); and thereafter
contacting said assembly with said
physiological fluid and measuring the $CO_2$ partial pressure (and optionally the $O_2$ partial pressure) in said physiological fluid.

Physiological fluids contemplated for analysis in accordance with the present invention include whole blood, blood plasma, blood serum, urine, dialysate, and the like.

"Suitable carbon dioxide sources" contemplated for use in the practice of the present invention are compounds which produce carbon dioxide upon introduction into an infusible saline solution. Examples of suitable carbon dioxide sources include sodium carbonate, sodium bicarbonate, calcium carbonate, ascorbic acid, ascorbate, and derivatives thereof, such as, for example, the the ascorbic acid derivatives described by Satoh et al., in U.S. Pat. No. 5,194,445, incorporated by reference herein.

Figure 2:
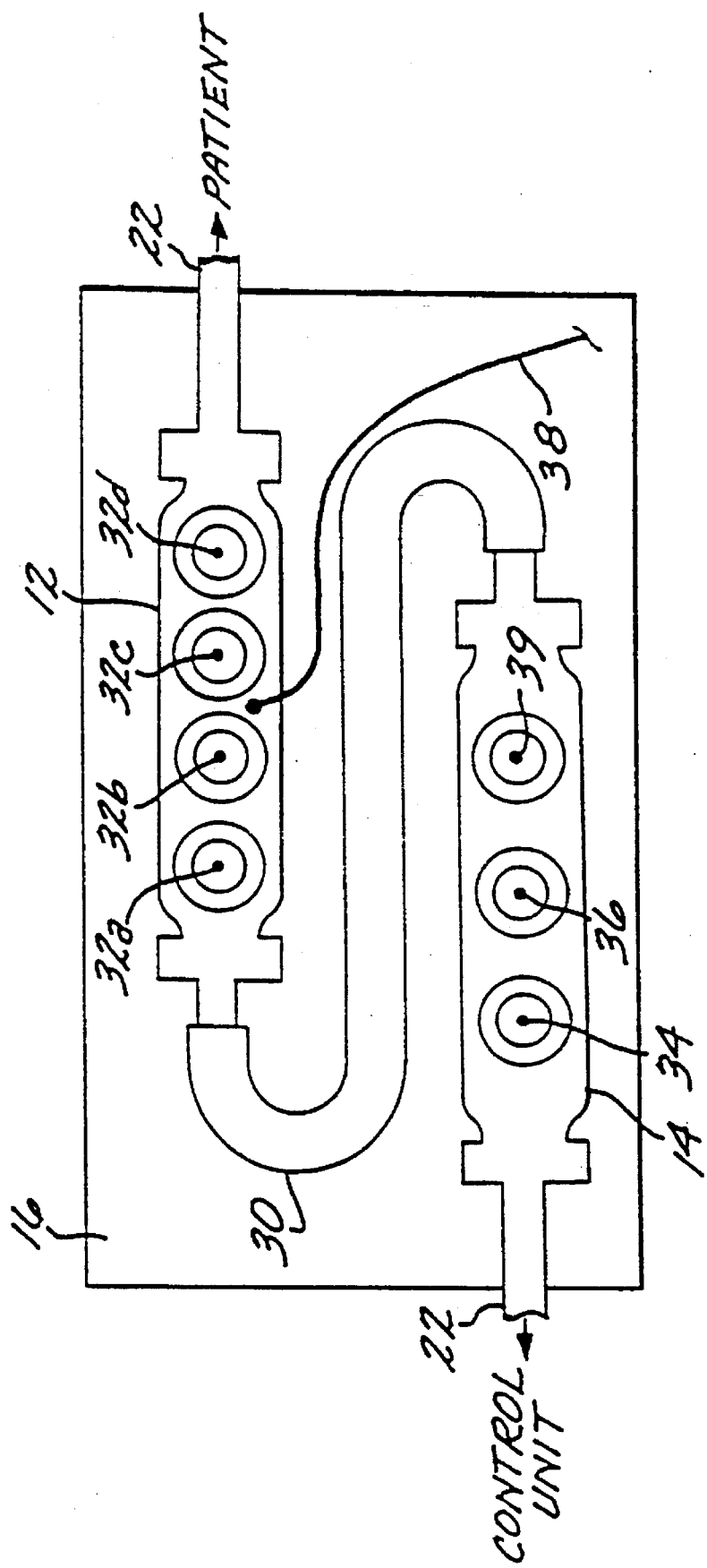
FIG. 2 is a plan view of a reference/sensor electrode assembly useful in the practice of the present invention.

Sensor assemblies contemplated for use in the practice of the present invention include indwelling (i.e., intravascular) catheter-based fiber optical blood gas sensors (such as are available from Puritan-Bennett, Optex, Biomedical Sensors, and the like); extracorporeal blood gas sensors (such as are available from 3M/CDI, Biomedical Sensors, Mallinckrodt, and the like); etc, as well as the sensor assembly shown in FIG. 2.

Calibrants contemplated for use in the practice of the present invention are typically non-buffered solutions, or, if buffered, weakly buffered so as not to preclude the use of invention calibrants as infusion medium. Such calibrants include:

physiological sodium chloride-containing saline, further containing an amount of a suitable carbon dioxide source effective to provide a stable $CO_2$ partial pressure in the range of about 1 up to 100 mm Hg, and optionally a stable $O_2$ partial pressure in the range of about 0 up to 200 mm Hg, optionally containing one or more additional electrolytes, 0.9% sodium chloride containing an amount of a suitable carbon dioxide source effective to provide a stable $CO_2$ partial pressure in the range of about 1 up to 100 mm Hg, and optionally a stable $O_2$ partial pressure in the range of about 0 up to 200 mm Hg, optionally containing one or more additional electrolytes, Isolyte™ brand infusible injection solution (available from Kendall McGaw, Irvine, Calif.) containing an amount of a suitable carbon dioxide source effective to provide a stable $CO_2$ partial pressure in the range of about 1 up to 100 mm Hg, and optionally a stable $O_2$ partial pressure in the range of about 0 up to 200 mm Hg, PlasmaLyte™ brand infusible injection solution (available from Baxter Healthcare Corporation, Chicago, Ill.) containing an amount of a suitable carbon dioxide source effective to provide a stable $CO_2$ partial pressure in the range of about 1 up to 100 mm Hg, and optionally a stable $O_2$ partial pressure in the range of about 0 up to 200 mm Hg, Ringer's injection containing an amount a suitable carbon dioxide source effective to provide a stable $CO_2$ partial pressure in the range of about 1 up to 100 mm Hg, and optionally a stable $O_2$ partial pressure in the range of about 0 up to 200 mm Hg, Ringer's Acetate containing an amount of a suitable carbon dioxide source effective to provide a stable $CO_2$ partial pressure in the range of about 1 up to 100 mm Hg, and optionally a stable $O_2$ partial pressure in the range of about 0 up to 200 mm Hg, Ringer's Lactate containing an amount of a suitable carbon dioxide source effective to provide a stable $CO_2$ partial pressure in the range of about 1 up to 100 mm Hg, and optionally a stable $O_2$ partial pressure in the range of about 0 up to 200 mm Hg, and the like.

The pCO2, $pO_2$ and pH levels of several of the above-described calibration/injection solutions are summarized below:

| Composition | $pCO_2$ (37° C.) (mm Hg) | $pO_2$ (37° C.) (mm Hg) | pH (37° C.) |
|---|---|---|---|
| Lactated Ringer's | 0.2–0.6 | 185 | 6.20 ± 0.5 |
| Lactated Ringer's with 20 mM/L $NaHCO_3$ | 8.0 | 185 | 8.05 |
| Lactated Ringer's with 20 mM/L $NaHCO_3$ and 0.05 mM/L EDTA | 9.0 | 185 | 7.95 |
| Lactated Ringer's with 20 mM/L $NaHCO_3$, 1 mM/L $Na_2HPO_4$ and 2 mM/L $NaH_2PO_4$ | 55 | 185 | 7.10 |
| Lactated Ringer's containing 5% L-ascorbic acid | 7–10 | 0–5 | 6.0 |
| Lactated Ringer's containing 5% L-ascorbate | 40 | 0–5 | 8.0 |

Sodium bicarbonate injection solutions useful in the invention process are readily available, typically at 8.4 w/w %, 7 w/w %, or 4.2 w/w %. Sodium bicarbonate injection solutions may also optionally contain stabilizing agent(s), which may act as pH regulating agents as well. The presence of stabilizing agents is frequently desirable because the $pCO_2$ level of an injection solution is a function of the pH of the injection solution, as well as the $HCO_3^-$ concentration used.

Ascorbic acid (or ascorbate) injection solutions useful in the invention process are readily available, typically at 10–50 w/w %; for example, Cevalin™, available from Eli Lilly & Co., is provided as an ascorbate solution containing 10–50 w/w % ascorbate, or Cenolate™, available from Abbott Laboratories, Inc., is provided as a 10 w/w % ascorbate-containing solution. Ascorbic acid injection solutions may also optionally contain pH regulating agents.

Electrolyte injections such as Ringer's Injection, Ringer's Acetate, and Ringer's Lactate contain fixed levels of $Na^+$, $Cl^-$, $K^+$ and $Ca^{++}$ and can be readily used to calibrate the corresponding sensors. Although I.V. saline solutions with dextrose are widely used in hospitals, most pre-mixed dextrose-containing I.V. solutions are 20–100 times too concentrated for use as a calibrant for blood glucose measurement. Fortunately, sterile dextrose injection solutions (typically 10 w/w % or higher) are widely available. A small amount of such an injection can be added to Ringer's Lactate (e.g., 10 ml of 10 w/w % dextrose per 1,000 ml) to provide a calibration point closer to the normal blood glucose level (i.e., 100 milligram per deciliter).

Since hematocrit is an ac impedance measurement, in principle, it only requires a single calibration point to establish the constant of the conductivity cell. This can easily be done with glucose-containing Ringer's Lactate since its conductivity is fixed as long as the temperature is known.

As for $pO_2$, since Ringer's Lactate is generally in equilibrium with the atmosphere at ambient temperature in most clinical settings, the amount of dissolved oxygen can be derived if the temperature and barometric pressure are available. This can readily be accomplished by one of skill in the art. Alternatively, an oxygen scavenger such as ascorbic acid can be employed to decrease or deplete the oxygen tension of a given solution. The oxygen tension in a situation where an oxygen scavenger has been added can readily be determined by reference to a calibration curve, or a sufficient amount of oxygen scavenger can be employed to ensure substantially complete removal of oxygen from the solution, i.e., $pO_2$ approaches zero.

In accordance with the present invention, it has been found, for example, that adding a small amount of sodium bicarbonate (i.e., 10 ml of 8.4% $NaHCO_3^-$) to a 500 ml bag of Ringer's Lactate could stabilize the pH and $pCO_2$ thereof for many hours (up to about 18 hours or longer) at pH=7.95 and $pCO_2$=9 mm Hg (when the pH and $pCO_2$ is measured at 37° C.). By adding other pH regulating agents, such as for example, sodium or potassium phosphate, to lower the pH to approximately 7.10, it would be possible to maintain the $pCO_2$ level at above 55 mm Hg.

Furthermore, the addition of a suitable $CO_2$ source (such as sodium bicarbonate) to injection solutions, such as Ringer's Lactate, does not significantly affect other parameters, for at least several days. Therefore, it is possible to use such a fluid to calibrate the entire multi-sensor array. The invention calibration solutions, therefore, make it possible to have a single infusible liquid calibrant for combinations of one or more of $Na^+$, $Cl^-$, $K^+$, $Ca^{++}$, $Mg^{++}$, pH, $pO_2$, glucose, lactate and pH sensors, in addition to $pCO_2$.

Those of skill in the art recognize that a variety of optional components can be included in the calibration solutions employed in the practice of the present invention. For example, in the range of about 10 up to 10,000 mg/L of dextrose can be included as a calibrant for glucose. It is also frequently desirable to include in the range of about 10 up to 50,000 IU/L sodium heparin in the infusion medium/calibrant. It is also frequently desirable to include pH regulating reagents in the infusion medium/calibrant. Exemplary pH regulating reagents include sodium or potassium phosphates, sodium or potassium acetates, sodium or potassium citrates, EDTA (ethylenediaminetetraacetic acid), and the like.

The pH, $pCO_2$ and $pO_2$ levels of calibration solutions employed in the practice of the present invention remain more or less constant in the I.V. bag because the plastic bag materials from which I. V. bags are constructed are generally relatively gas impermeable. However, the I. V. solution administration set, particularly the peristaltic pumping segment, may not be as gas-tight. As the solution travels along the I. V. line towards the sensors and the vascular access port, some $CO_2$ will likely be lost, and $O_2$ will tend to equilibrate with ambient $pO_2$, especially when the fluid sits almost stagnant over the sensors (for example, when the monitor is in standby mode). This problem can readily be addressed in a variety of ways, for example, by taking advantage of the fluid handling capability of the infusion system. Periodically, a certain amount of solution (e.g., 5 ml) may be pumped into the patient in order to bring fresh solution from the bag to the sensors for calibration.

However, it may be impractical, or clinically undesirable, to infuse large amounts of I.V. fluids into a patient over a given period of time, especially for neonates, infants, fluid-restricted patients, and the like. An alternative means to compensate for small changes in calibrant $pCO_2$ levels (as a result of $CO_2$ leakage, temperature fluctuations, and the like) is based on the fact that for a given $HCO_3^-$-containing I.V. solution, the relation between pH and $CO_2$ is well defined. For example, as presented above, the pH of a simple bicarbonate-containing solution at 37° C. is $$6.10 + \log\{[HCO_3^-]/0.0301\ pCO_2\}$$

In an aqueous solution containing other compounds (e.g., sodium, potassium, calcium, magnesium, chloride, glucose, and the like), it is still possible to model the relationship between pH and $pCO_2$ (based on the above theoretical relationship), and experimentally verify the results. Thus, small fluctuations in $pCO_2$ in calibrant which is in contact with the $pCO_2$ sensor may be corrected by monitoring the pH on a continuous basis. This can be accomplished, for example, using the pH sensor in sensor assembly 12 (shown in FIG. 2). However, because the pH sensor in sensor assembly 12 is periodically exposed to physiological fluid, it may drift slightly over time, due primarily to the possibility of the buildup of a thin protein layer thereon. Accordingly, it is presently preferred to use a separate pH sensor (which is constantly exposed to calibrant only) to provide much more reliable results. To this end, electrode 39 in reference assembly 14, as shown in FIG. 2, is provided as a pH sensor specifically for this purpose. Observed changes in pH can then be used to correct the calibration points for pH and $pCO_2$ for the measurements taken shortly thereafter.

Oxygen partial pressure can readily be determined by reference to a calibration curve. Thus, as noted above, the $pO_2$ of physiological saline is substantially higher than typical blood oxygen levels. Addition of an oxygen scavenger, such as ascorbic acid, ascorbate, and derivatives thereof, would reduce oxygen levels substantially, to levels much more in the range of normal physiological values. The $pO_2$ for a given blood sample can readily be determined by reference to a calibration curve, or a sufficient amount of oxygen scavenger can be employed to ensure substantially complete removal of oxygen from the solution.

In accordance with another embodiment of the present invention, there are provided physiological saline solutions suitable for infusion into a subject, and simultaneously suitable for calibration of sensors capable of detecting $pCO_2$ without introduction of $CO_2$ gas therein, and optionally capable of detecting $pO_2$ without introduction of $O_2$ gas therein, said solution comprising:

physiological sodium chloride-containing saline, and an amount of a suitable carbon dioxide source effective to provide a stable $CO_2$ partial pressure in the range of about 1 up to 100 mm Hg, and optionally a stable $O_2$ partial pressure in the range of about 0 up to 200 mm Hg.

In accordance with a presently preferred embodiment of the present invention, a single infusible calibrant is employed which enables the substantially simultaneous calibration of a multi-sensor assembly comprising a plurality of sensors, wherein the plurality of sensors are responsive to one or more additional species selected from $Na^+$, $K^+$, $Ca^{++}$, $Mg^{++}$, $Cl^-$, pH, glucose and lactate, in addition to $pCO_2$ (and optionally $pO_2$). Multi-sensor assemblies capable of detecting (i.e., responsive to) two or more of the above-identified species have been developed for use in association with suitable ex vivo blood chemistry monitors.

In accordance with another embodiment of the present invention, there is provided an improved combination infusion delivery system and chemical analysis system having a sensor capable of determining $CO_2$ partial pressure, and optionally, a sensor capable of determining $O_2$ partial pressure, in physiological fluid, wherein physiological saline is employed as the infusion medium, the improvement comprising introducing an amount of a suitable carbon dioxide source into said physiological saline effective to provide a stable $CO_2$ partial pressure and optionally a stable $O_2$ partial pressure adequate to calibrate said $CO_2$ and said $O_2$ sensor. Typically, an effective amount of a suitable carbon dioxide source is an amount effective to provide a stable $pCO_2$ in the range of about 1 up to 100 mm Hg, and a stable $pO_2$ in the range of about 0 up to 200 mm Hg in said physiological saline solution.

In accordance with yet another embodiment of the present invention, there is provided a method for the calibration of a sensor employed for the detection of $CO_2$ partial pressure, and optionally, $O_2$ partial pressure, in physiological fluid, said method comprising contacting a sensor assembly having:
a fluid passageway and a sensor for $CO_2$, and optionally a sensor for $O_2$, exposed to said fluid passageway, and
means to pass physiological fluid and/or calibrant over said sensor,
with an infusion medium/calibrant comprising:
physiological sodium chloride-containing aqueous saline, and
an amount of a suitable carbon dioxide source effective to provide a stable $CO_2$ partial pressure in the range of about 1 up to 100 mm Hg, and optionally a stable $O_2$ partial pressure in the range of about 0 up to 200 mm Hg; and thereafter calibrating said sensor.

Control system(s) employed in the practice of the present invention preferably control the flow of fluids so that infusion fluid is used for calibration and, during calibration, is made to flow at a predetermined flow rate through the electrode assembly. When blood is drawn up into the infusion line, it is made to flow past the sensing electrode during measurement at substantially the same predetermined flow rate as during calibration. This eliminates any effect fluid flow rate might otherwise have on the measurements. Further, the electrode assembly can be used for both a reference assembly having a reference electrode and a sensor assembly having one or more sensing electrodes, with the reference assembly and sensor assembly mounted side-by-side in a compact unit that is easy to remove and replace.

The infusion/analysis system employed in accordance with the present invention calibrates during infusion and takes measurements of blood chemistry during the time that fluid sample drawn into the infusion line is being reinfused into the patient.

The reference electrode and sensing electrodes can be provided in separate assemblies for a blood chemistry measurement system, placed side-by-side in a compact unit. Placing the reference and sensor assemblies in a single unit provides an assembly that is more comfortable for the patient, facilitates removal and replacement of the assemblies, and also allows more precise calibration of the blood volume withdrawn and fluid infused, providing increased accuracy and reliability. For example, the time needed for the desired amount of blood to be withdrawn into the sensor assembly can be calculated and an error condition can be signalled if this time is exceeded with no indication of blood in the assembly. The diameter of the infusion line between the assemblies can be enlarged, reducing the electrical resistance of the fluid between the assemblies and providing more accurate readings.

A temperature sensing electrode (e.g., a thermistor or thermal couple) can be provided with the sensing electrodes, to provide a temperature signal that can be used to correct the sensed readings to compensate for changes in temperature. Furthermore, an additional electrode can be provided to act as a key to the controller to signal what particular types of sensors are provided in the assembly. For example, standardized groupings of sensors can be provided, and the keying electrode can cause the controller to act appropriately for the group of sensors provided.

Figure 1:
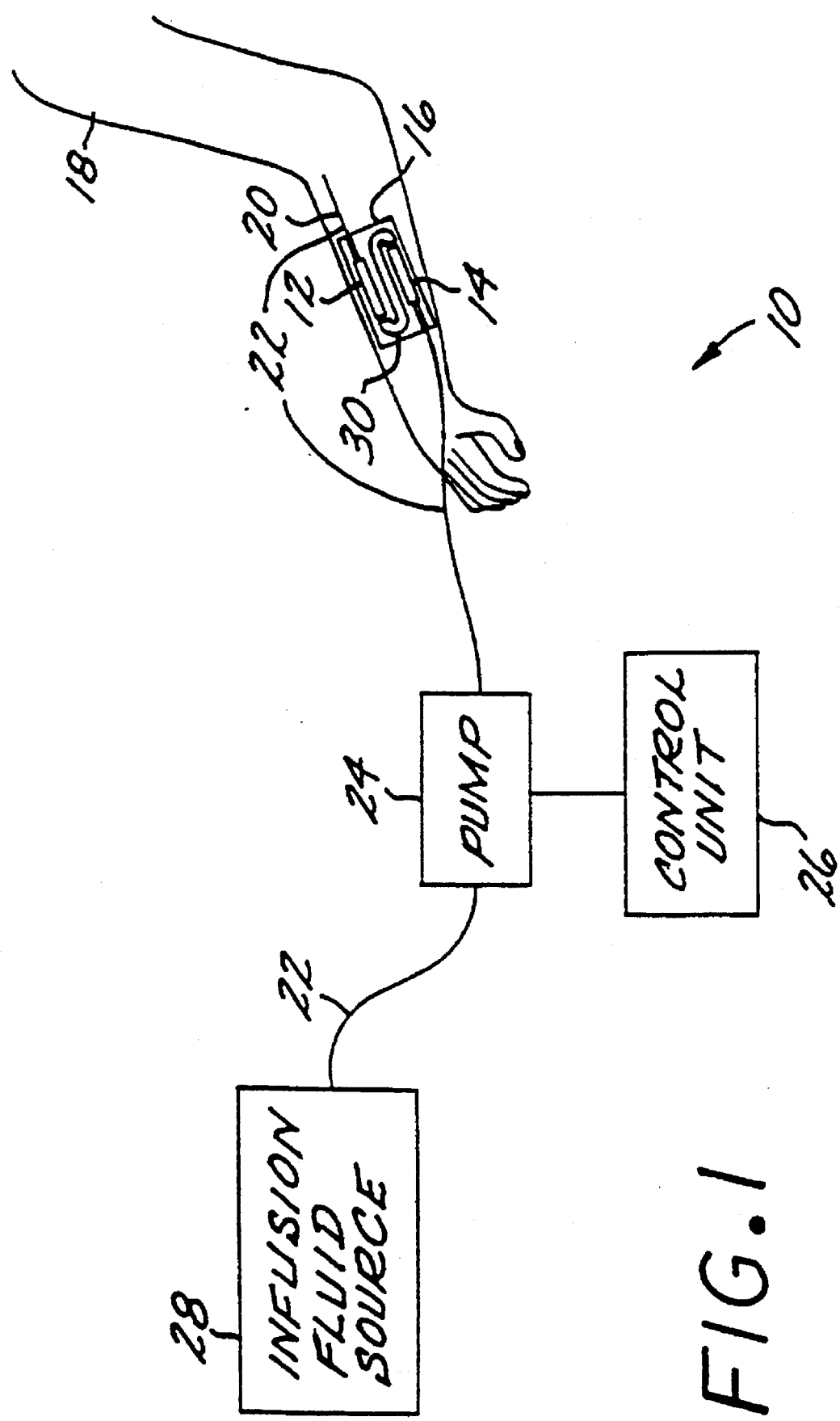
FIG. 1 is a schematic diagram of a combination infusion fluid delivery and blood chemistry analysis system useful in the practice of the present invention.

In a presently preferred embodiment of the present invention, the combination infusion fluid delivery system and blood chemistry analysis system illustrated in FIG. 1 is employed. System 10 of FIG. 1 includes a sensor assembly 12 and a reference assembly 14 having electrodes constructed as described in U.S. patent application Ser. No. 07/581,803, filed Sep. 13, 1990, issued as U.S. Pat. No. 5,165,406 (Nov. 24, 1992), the two assemblies being mounted side-by-side on an arm board 16 that is attached to a patient 18. While the assembly includes a separate sensor assembly and reference assembly, and therefore is suited to a differential measurement system, it is to be understood that the assemblies could be integrated into a single unit to operate in a non-differential measurement system. The sensor assembly 12 is connected to the patient via an intravenous (IV) port 20 and an infusion line 22, which continues upstream of the sensor assembly to the reference assembly 14 and then to a peristaltic pump 24 that is controlled by a control unit 26. Those skilled in the art will appreciate that the pump and control unit can alternatively be integrated into a single unit. Finally, the infusion line 22 continues upstream of the pump to an infusion fluid source 28.

During calibration of system 10, control unit 26 controls pump 24 and meters infusion fluid from the infusion fluid source 28, through the pump, past reference assembly 14, past sensor assembly 12, and into the patient 18. The reference and sensor assemblies preferably include electrodes constructed as described in U.S. Pat. No. 5,165,406, and during calibration, the electrical potential between respective electrodes of the two assemblies is measured to provide a series of calibration measurements for system 10.

During a measurement mode of the system, blood is withdrawn from the patient 18 into infusion line 22 past sensor assembly 12 but not up to reference assembly 14, as described further below, and the electrical potential between respective electrodes is again measured. The electrical potential will be changed from the calibration measurements, and the difference corresponds to a calculated amount of a particular ion in the patient's blood. Sensor assembly 12 can include, for example, sensors that are sensitive to blood chemistry ions including calcium, hydrogen, chloride, potassium, sodium, $CO_2$ partial pressure, $O_2$ partial pressure, and the like.

Substantially the same flow rates are used in the infusion line through the electrode assembly when infusion fluid flows during calibration as when blood flows during measurement. More particularly, the control system controls the infusion pump of the combined infusion fluid delivery and blood chemistry measurement system such that the infusion fluid is pumped past the reference and sensor electrodes at a fixed flow rate during calibration, and the blood measurement is taken while the blood is infused back into the patient at approximately the same flow rate.

As shown in FIG. 2, the sensor electrode assembly 12 and the reference electrode assembly 14 contain electrodes that are constructed in accordance with the present invention. The assemblies are in flow communication via a connecting conduit 30 in the infusion line 22. The sensors in the sensor assembly have one or more sensing electrodes (illustrated in the Figure with four sensors, i.e., 32a, 32b, 32c, and 32d). Each sensor reacts with fluid in the assembly and generates a voltage signal relative to the reference assembly 14. Those of skill in the art recognize that the number of sensing electrodes included in the sensor assembly can vary widely. Thus, in the range of one up to ten sensors or more can be employed in the practice of the present invention. One of the reference assembly's electrodes 34 is used as patient or solution ground, and are connected to what is known as an isolated ground (not illustrated). A second reference electrode 36 is a common reference for the sensor electrodes. That is, the sensor electrode electrical signals are with respect to the common reference, thereby providing differential measurement.

A temperature sensing line 38 is provided from a built-in thermistor (located in sensor assembly 12) to the control unit 26. The temperature sensing line provides the control unit with a signal that represents the temperature of the calibration fluid. This information is used to calibrate the output signals from the electrodes to give more accurate blood chemistry readings. Finally, a third electrode 39 is a pH sensor which is dedicated to monitoring the pH of the calibrant on a continuous basis. Any changes in pH detected will be used to correct the pH and $pCO_2$ calibration points.

Presently preferred electrode assemblies useful in the practice of the present invention are described in U.S. Pat. No. 5,165,406.

The combination infusion fluid delivery system and blood chemistry analysis system of FIG. 1 referred to previously includes the sensor assembly 12 having various electrodes sensitive to particular blood chemistry ions, such as calcium, hydrogen, chloride, potassium, sodium, and the like, and is preferably constructed in accordance with the assembly described in U.S. Pat. No. 5,165,406. As shown in FIGS. 1 and 2, the sensor assembly 12 and reference assembly 14 are in flow communication, separated by a connecting loop 30 of the infusion line 22 that is approximately four to six inches in length. The connecting loop advantageously has a larger internal diameter than the remainder of the infusion line 22. The larger diameter facilitates cleaning the line of bubbles and reduces the electrical resistance of the fluid between the electrodes. The reduced resistance increases the accuracy of measurement.

During the measurement mode of operation, the delivery of infusion fluid from the infusion fluid source 28 into the patient is halted. The direction of flow of the infusion fluid in line 22 is then reversed. That is, infusion fluid in the line is pumped back into the fluid source. This process eventually withdraws blood from the patient into infusion line 22 past sensor assembly 12 and into connecting loop 30, but not far enough to reach the level of reference assembly 14. This is a volume of approximately 0.5–1.0 cc of blood.

After the blood is drawn into line 22, it remains in place for approximately 15 to 20 seconds while the system stabilizes. During this period, the blood in the infusion line is reinfused into the patient 18 be under control of control unit 26 at approximately the same rate as that at which the infusion fluid was earlier delivered into the patient during calibration. After a short time interval of reinfusion, for stabilization of the sensors, the potential differences between the respective electrodes of reference assembly 14 and sensor assembly 12 are measured and provided to control unit 26. Making the blood chemistry measurements at a blood flow rate equal to that of the earlier calibrating flow rate eliminates any effect on the measurements that the fluid flow might otherwise have. This yields an accurate reading of the blood chemistry parameters.

The sensor assembly may be thermostatted at about 37° C. (for example, by being positioned inside an electrically heated enclosure). Any deviation from the target temperature of 37° C. will be detected by temperature sensing line 38. Temperature sensing line 38 provides control unit 26 with an indication of the temperature at which the analytical measurement is carried out. The measured electrical potential from the various electrodes will change with temperature such that temperature changes in calibration fluid from the time of calibration to the time of measurement can provide inaccurate data. Therefore, the control unit can use the temperature information to adjust the blood chemistry readings to compensate for the changes in temperature, providing increased accuracy and reliability. In addition, the temperature information provided by sensor 38 can also be used as part of a feedback control system for control of the heater used to heat the sensor assembly.

Eventually, after the blood chemistry measurements have been completed and the blood sample has been reinfused into the patient 18, additional infusion fluid drawn from fluid source 28 proceeds through both infusion line 22 and sensor assembly 12 and back into the patient. Control unit 26 continues the flow of infusion fluid until a purge volume of fluid, roughly eight to ten times that of the drawn blood, has passed through the sensor assembly. This takes approximately two minutes. Thus, the control unit allows measurements to be taken as frequently as at approximately two minute intervals.

It should be appreciated that the present invention provides an easily prepared calibration solution that allows for the simultaneous calibration of both gaseous and non-gaseous species in physiological fluid. The control unit of a combined infusion fluid delivery and blood chemistry analysis system employed in accordance with the present invention ensures that the fluid flow rate through the sensor assembly is approximately the same during calibration and during measurement. This eliminates the effect of fluid flow and turbulence on the measurements.

While the invention has been described in detail with reference to certain preferred embodiments thereof, it will be understood that modifications and variations are within the spirit and scope of that which is described and claimed.

That which is claimed is:

1. A method for the calibration of a sensor employed for the detection of $CO_2$ partial pressure ($pCO_2$), and optionally, $O_2$ partial pressure ($pO_2$), in physiological fluid, said method comprising
    contacting a sensor assembly having:
        a fluid passageway and a sensor for $pCO_2$, and optionally a sensor for $pO_2$, exposed to said fluid passageway, and
        means to pass physiological fluid or calibrant or both over said sensor,
    with an infusion medium/calibrant comprising:
        non-buffered physiological sodium chloride-containing saline, and
        an amount of a carbon dioxide source effective to provide a stable $pCO_2$ in the range of about 1 up to 100 mm Hg, and optionally a stable $pO_2$ in the range of about 0 up to 200 mm Hg, and thereafter calibrating said sensor.

2. A method according to claim 1 wherein said method further comprises the concurrent calibration of $pO_2$ and $pCO_2$.

3. A method according to claim 2 wherein said method further comprises the calibration of one or more additional species selected from $Na^+$, $K^+$, $Ca^{++}$, $Mg^{++}$, $Cl^-$, hydrogen ions, lactose or glucose, or combinations of any two or more thereof, in addition to $pO_2$ and $pCO_2$.

4. A method according to claim 3 wherein said calibration is carried out employing a multi-sensor assembly comprising a plurality of sensors which are responsive to one or more additional species selected from $Na^+$, $K^+$, $Ca^{++}$, $Mg^{++}$, $Cl^-$, hydrogen ions, lactose or glucose, or combinations of any two or more thereof, in addition to $O_2$ and $CO_2$.

5. A method according to claim 1 wherein said method further comprises the calibration of one or more additional species selected from the group consisting of $Na^+$, $K^+$, $Ca^{++}$, $Mg^{++}$, $Cl^-$, pH, lactate and glucose, in addition to $pCO_2$.

6. A method according to claim 5 wherein said calibration is carried out employing a multi-sensor assembly comprising a plurality of sensors which are responsive to one or more additional species selected from $Na^+$, $K^+$, $Ca^{++}$, $Mg^{++}$, $Cl^-$, hydrogen ions, lactose or glucose, or combinations of any two or more thereof, in addition to $CO_2$.

7. A method according to claim 1 wherein said infusion medium/calibrant is selected from:

non-buffered physiological sodium chloride-containing saline, further containing an amount of a carbon dioxide source effective to provide a stable $CO_2$ partial pressure in the range of about 1 up to 100 mm Hg, and optionally a stable $O_2$ partial pressure in the range of about 0 up to 200 mm Hg, optionally containing one or more additional electrolytes, non-buffered 0.9% sodium chloride containing an amount of a carbon dioxide source effective to provide a stable $CO_2$ partial pressure in the range of about 1 up to 100 mm Hg, and optionally a stable $O_2$ partial pressure in the range of about 0 up to 200 mm Hg, optionally containing one or more additional electrolytes, non-buffered Isolyte™ brand infusible injection solution containing an amount of a carbon dioxide source effective to provide a stable $CO_2$ partial pressure in the range of about 1 up to 100 mm Hg, and optionally a stable $O_2$ partial pressure in the range of about 0 up to 200 mm Hg, non-buffered PlasmaLyte™ brand infusible injection solution containing an amount of a carbon dioxide source effective to provide a stable $CO_2$ partial pressure in the range of about 1 up to 100 mm Hg, and optionally a stable $O_2$ partial pressure in the range of about 0 up to 200 mm Hg, non-buffered Ringer's injection containing an amount of a carbon dioxide source effective to provide a stable $CO_2$ partial pressure in the range of about 1 up to 100 mm Hg, and optionally a stable $O_2$ partial pressure in the range of about 0 up to 200 mm Hg, non-buffered Ringer's Acetate containing an amount of a carbon dioxide source effective to provide a stable $CO_2$ partial pressure in the range of about 1 up to 100 mm Hg, and optionally a stable $O_2$ partial pressure in the range of about 0 up to 200 mm Hg, or non-buffered Ringer's Lactate containing an amount of a carbon dioxide source effective to provide a stable $CO_2$ partial pressure in the range of about 1 up to 100 mm Hg, and optionally a stable $O_2$ partial pressure in the range of about 0 up to 200 mm Hg.

8. A method according to claim 7 wherein said infusion medium/calibrant further comprises in the range of about 10 up to 10,000 mg/L of dextrose.

9. A method according to claim 7 wherein said infusion medium/calibrant further comprises in the range of about 10 up to 50,000 IU/L sodium heparin.

10. A method according to claim 7 wherein said infusion medium/calibrant further comprises one or more non-buffering pH adjusting reagents.

11. A method according to claim 1 wherein said method further comprises passing a volume of calibrant through the fluid passageway of said sensor assembly sufficient to provide contact of fresh calibrant with at least one of said sensors when calibrating.

12. A method according to claim 1 wherein said method further comprises determining the time required for transport of fluid from the source container to the sensor, and correcting the calibration of said system to reflect the diffusion loss of gases to which the tubing employed for delivery of infusible fluid is permeable.

13. A method according to claim 1 wherein said method further comprises compensating for changes in the $pCO_2$ in the calibrant by monitoring any changes in the pH and/or temperature of the calibrant and calculating the resulting $pCO_2$ based on the pH of the calibrant.

14. A method for the assay of $CO_2$ partial pressure ($pCO_2$), and optionally $O_2$ partial pressure ($pO_2$), in physiological fluid, said method comprising contacting an assembly having:
a fluid passageway and a sensor for $pCO_2$, and optionally a sensor for $pO_2$, exposed to said fluid passageway, and
means to pass physiological fluid or calibrant or both over said sensor, with an infusible calibrant comprising:
non-buffered physiological sodium chloride-containing saline, and
an amount of a carbon dioxide source effective to provide a stable $pCO_2$ in the range of about 1 up to 100 mm Hg, and optionally a stable $pO_2$ in the range of about 0 up to 200 mm Hg; and calibrating said $pCO_2$ sensor; and thereafter contacting said assembly with said physiological fluid and measuring the $pCO_2$ in said physiological fluid.

15. In a method for the assay of $pCO_2$, and optionally, $pO_2$, in physiological fluid employing a sensor assembly, the improvement comprising using an infusible calibrant comprising:
non-buffered physiological sodium chloride-containing saline, and
an amount of a carbon dioxide source effective to provide a stable $pCO_2$ in the range of about 1 up to 100 mm Hg, and optionally a stable $pO_2$ in the range of about 0 up to 200 mm Hg.

16. In a combination infusion delivery system and chemical analysis system having a sensor which determines $CO_2$ partial pressure ($pCO_2$), and optionally, a sensor which determines $O_2$ partial pressure ($pO_2$), in physiological fluid, wherein physiological saline is employed as the infusion medium, the improvement comprising introducing an amount of a carbon dioxide source into said physiological saline effective to provide a stable $pCO_2$ and optionally a stable $pO_2$ to calibrate said $CO_2$ and optionally said $O_2$ sensor.

* * * * *